United States Patent [19]

Saito et al.

[11] Patent Number: 4,913,697

[45] Date of Patent: Apr. 3, 1990

[54] THERMOSETTING RESIN COMPOSITION FROM ALKENYLARYLOXY TRIAZINE

[75] Inventors: Yasuhisa Saito, Higashiosaka; Kunimasa Kamio, Suita; Shuichi Kanagawa, Niihama; Yutaka Shiomi, Hirakata, all of Japan

[73] Assignee: Sumitomo Chemical Company, Limited, Osaka, Japan

[21] Appl. No.: 281,458

[22] Filed: Dec. 8, 1988

Related U.S. Application Data

[62] Division of Ser. No. 45,431, May 4, 1987, Pat. No. 4,808,717.

[30] Foreign Application Priority Data

Sep. 17, 1986 [JP] Japan ................................ 61-218757
Sep. 19, 1986 [JP] Japan ................................ 61-223455

[51] Int. Cl.$^4$ ............................................ C08G 63/38
[52] U.S. Cl. ..................... 528/205; 524/611; 524/612; 528/86; 528/125; 528/211; 528/219; 528/392; 528/423
[58] Field of Search ............... 528/205, 211, 219, 125, 528/86, 392, 423

[56] References Cited

U.S. PATENT DOCUMENTS

| 4,100,140 | 7/1978 | Zahir et al. | 526/173 |
| 4,127,615 | 11/1978 | Zahir et al. | 525/502 |
| 4,808,717 | 2/1989 | Saito et al. | 544/219 |

FOREIGN PATENT DOCUMENTS

| 52-994 | 1/1977 | Japan . |
| 53-134099 | 11/1978 | Japan . |
| 56-4610 | 1/1981 | Japan . |
| 58-27806 | 6/1983 | Japan . |
| 59-15126 | 4/1984 | Japan . |

*Primary Examiner*—Harold D. Anderson
*Attorney, Agent, or Firm*—Stevens, Davis, Miller & Mosher

[57] ABSTRACT

A thermosetting resin composition comprising (i) a polymaleimide compound having at least two maleimide groups in the molecule and (ii) an s-triazine compound having at least two alkenylaryloxy groups in the molecule; a resin-composition for encapsulant comprising said polymaleimide compound, said traizine compound, and an inorganic filler as essential components; and said s-triazine compound.

2 Claims, 6 Drawing Sheets

THERMOSETTING RESIN COMPOSITION FROM ALKENYLARYLOXY TRIAZINE

This is a division of application Ser. No. 045,431, filed May 4, 1987, now U.S. Pat. No. 4,808,717.

BACKGROUND OF THE INVENTION

1. Field of the Invention

The present invention relates to a thermosetting resin composition and more particularly to a thermosetting resin composition excellent in processability and heat resistance.

Further, the invention relates to a thermosetting resin which is a component of said thermosetting resin composition.

Furthermore, the invention relates to a resin composition using as encapsulant for electronic component which are applications of above mentioned thermosetting resin composition.

2. Description of the Prior Art

Thermosetting resins are in use as casting, impregnating, laminating, and molding materials for various electric insulations and structures. In recent years, there has been the tendency of material service conditions to more severity in these applications and the heat resistance of materials has become an important property.

Conventionally, thermosetting polyimide resins are used for these purposes but their processing requires long-time heating thereof at high temperatures.

Expoxy resins improved in heat resistance, although superior in processability, are insufficient in high-degree heat resistance including mechanical and electrical properties at high temperatures and long-term resistance to thermal degradation.

An example of possible substitutes for these materials is a type of thermosetting resin comprising both a monomer having a double bond and a maleimide compound, as disclosed in Japanese Patent Publication Nos. 27806/83 and 15126/84. However, this type of resin needs to be converted into a prepolymer before thermosetting, because the above-mentioned monomer has a low molecular weight. When the resin is thermoset directly without the prepolymer conversion, there arises the problem of partial monomer vaporization taking place during the hardening. When the double bond-containing monomer has only one double bond in the molecule, the density of crosslinkage in the cured resin is limited and the cured resin is insufficient in heat resistance.

Other materials proposed include for example, a thermosetting resin mixture comprising a polyimide and an alkenylphenol and/or an alkenyl phenol ether (Japanese Patent Application Laid-Open No. 994/77) and a heat-resistant resin composition comprising a maleimide compound, a poly(allylphenol) compound and an epoxy resin (Japanese Patent Application Laid-Open No. 134,099/78). These materials, however, have the problems of the cured products thereof exhibiting hihg permittivity and inferior water resistance, because the poly(allyl phenol) compound used in these materials in the Claisen rearrangement product of a poly(allyl ether) compound or has a structure which produces phenolic hydroxyl group through Claisen rearrangement during thermal curing. In addition, the ring-substituting allyl group and either the ring-substituting hydroxyl group or ether residue are situated in positions ortho to each other on an aromatic ring and are liable to remain unreacted after curing particularly when the poly(allyl phenol) compound is of a novolak type, thereby affecting adversely properties of the cured products of the materials at high temperatures.

SUMMARY OF THE INVENTION

Under such circumstances the present inventors made intensive studies with an object of providing a resin composition excellent in heat resistance and processability. As a result, it has been found that the above object can be achieved with a thermosetting resin composition which comprises (i) an s-triazine compound having at least two alkenylaryloxy groups in the molecule and (ii) a polymaleimide compound that has at least two maleimide groups in the molecule. Thus, the thermosetting resin composition has been developed, that is, an aspect of the present invention has been accomplished.

Common s-triazine compounds are found in crystalline or noncrystalline form. Having high melting points, crystalline s-triazine compounds suffer in processability or workability when used as such without any solvent. That is, in order to flow a crystalline s-triazine compound, it is necessary to maintain the compound at a temperature of at least 100° C., otherwise the compound is difficult to mix with a polymaleimide compound. Therefore, the present inventors searched for an s-triazine compound which is improved in processability and workability particularly in the undissolved state without sacrificing the excellent heat resistance, water resistance, and electrical properties of the resulting resin composition. As a result, a specific noncrystalline s-triazine compound (resin) having alkenyl groups and triazine rings has been discovered, which is represented by general formula (1) as described below. That is, it has been found that a thermosetting resin composition comprising this resin and a polymaleimide compound offers improved processability and workability while maintaining the intended heat resistance, water resistance, and electrical properties. Based on this finding, an invention relating to a resin, which is an embodiment of the present invention, has been accomplished.

Further, the present inventors also investigated crystalline s-triazine compounds which may be used for compounding the intended thermosetting resin composition. Thus a suitable crystalline compound for use in the thermosetting resin composition, that is, an aspect of the present invention, has been discovered from the fact that a thermosetting resin composition having excellent moldability can be obtained when a specific alkenyl group is used for substituting the aryloxy group of the compound represented by formula (2).

Moreover, the present inventors investigated applications of the present thermosetting resin composition using as encapsulant for electronic components therewith.

Heretofore, thermosetting resins have been used for encapsulating electronic components such as diodes, transistors, and integrated circuits.

This resin encapsulation (plastic mold) is applied extensively since it is economically advantageous over the hermetic sealing system employing glass, metal, or ceramic. Of resin compositions for encapsulant, epoxy resin compositions are most commonly used in view of the reliability and price. In recent years, conditions of applying these encapsulant have had a tendency to become severe similarly to those of applying other materials as mentioned above and particularly the heat resistance of materials has become an important property. Accordingly, the use of thermosetting polyimide resin compositions or epoxy resin compositions improved in heat resistance is contemplated but these materials have such problems as stated above.

That is, polyimide resin composition, although having high heat resistance, require long heating at high temperatures for processing and have a significant economical drawback.

Epoxy resin compositions improved in heat resistance, although superior in processability, are unsatisfactory in high-degree heat resistance including mechanical and electrical properties at high temperatures and long-term resistance to thermal degradation.

Under such circumstances, the present inventors made intensive studies with the object of providing a encapsulant excellent in heat resistance and processability. As a result, it has been found that the above object can be achieved with a resin composition comprising the above defined thermosetting resin composition and an inorganic filler as essential components. Based on this finding, an aspect of the present invention has been accomplished.

According to an aspect of the invention, there is provided a thermosetting resing composition comprising (i) an s-triazine compound having at least two alkenylaryloxy groups in the molecule and (ii) a polymaleimide compound having at least two maleimide groups in the molecule.

The s-triazine compound includes a resin represented by the general formula $$\left[\begin{array}{c} Y \\ N \overset{\|}{\diagup} N \\ Ar_1O \diagdown N \diagup OAr_2O \end{array}\right]_n \begin{array}{c} Y \\ N \overset{\|}{\diagup} N \\ \diagdown N \diagup OAr_1 \end{array} \quad (1)$$

wherein, n denotes numbers of 0 to 15, $Ar_1$ denotes a monovalent alkenylphenol residue, $Ar_2$ denotes a divalent phenol residue, and Y denotes $—OAr_1$ or another substituent. This resin (hereinafter referred to as resin A) has alkenyl groups and triazine rings and is characterized by containing at least 20% of components of formula (1) wherein n is at least 1 (resin A has such a distribution of n that fractions having n values of at least 1 amounts 20% of resin A).

The invention provides the above defined resin A as well.

According to another aspect of the invention, there is provided a crystalline s-triazine compound which gives a thermosetting resin composition having excellent moldability.

According to another aspect of the invention, there is provided resin composition for encapsulant comprising (i) an s-triazine compound having at least two alkenylaryloxy groups in the molecule, (ii) a polymaleimide compound having at least two maleimide groups in the molecule, and (iii) an inorganic filler, as essential components.

DETAILED DESCRIPTION OF THE INVENTION

Figure 1:
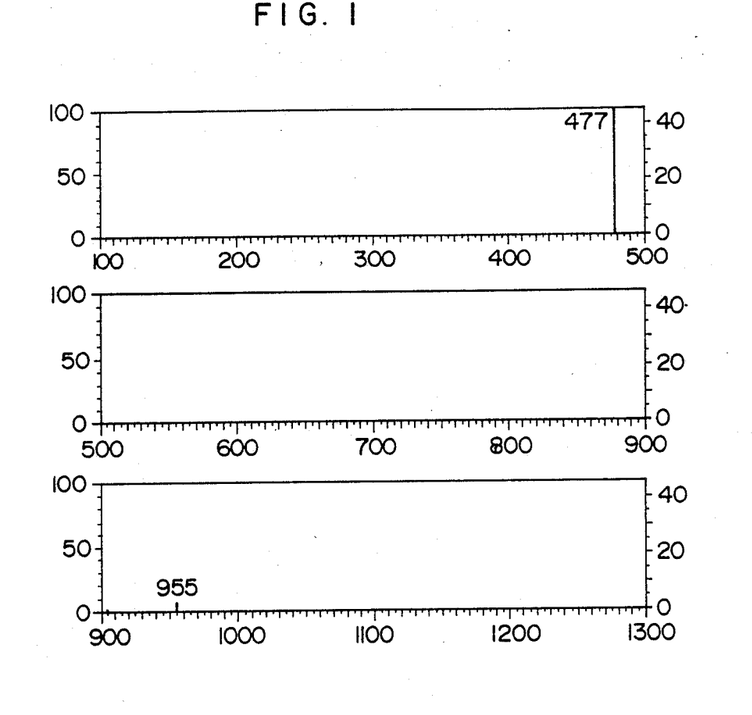
FIG. 1 shows FD-MS spectra of compounds prepared in Example 1.
Figure 2:
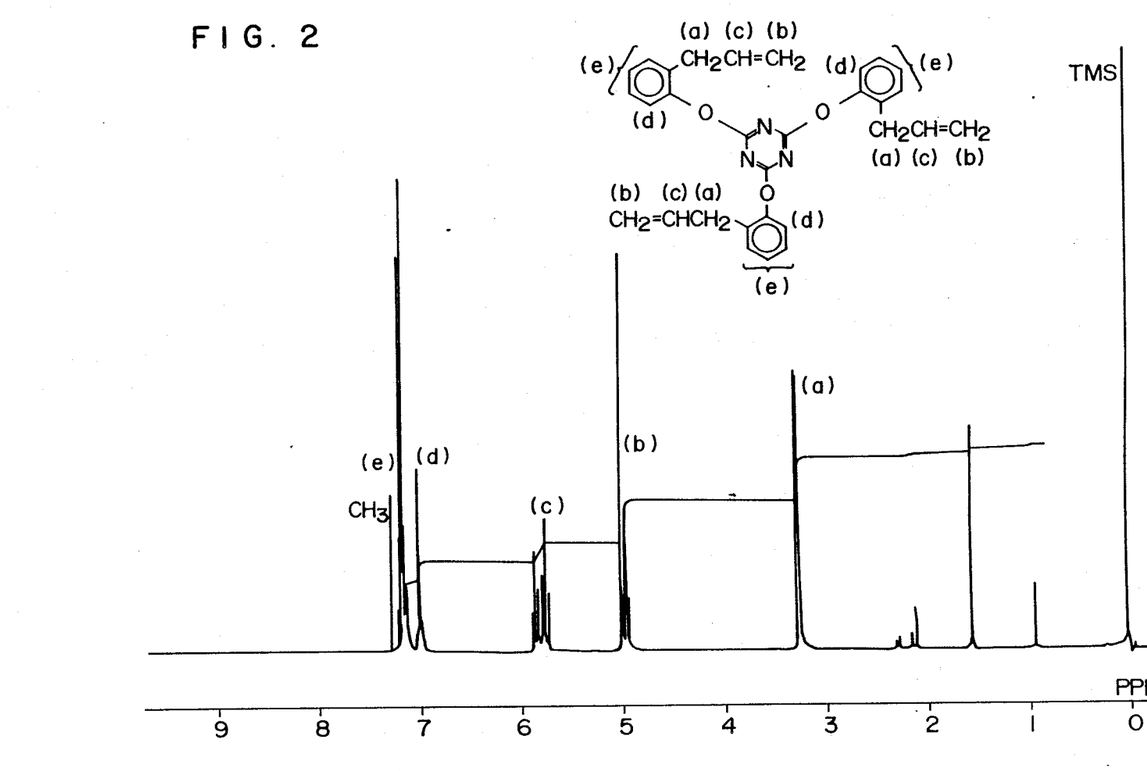
FIG. 2 shows an NMR spectrum of a compound prepared in Example 1.
Figure 3:
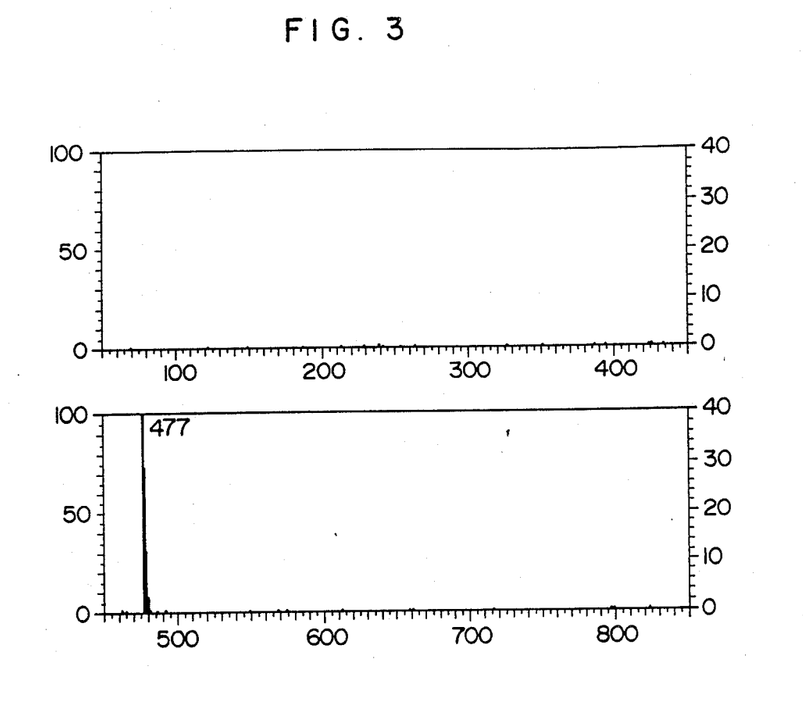
FIG. 3 shows FD-MS spectra of compounds prepared in Example 2.
Figure 4:
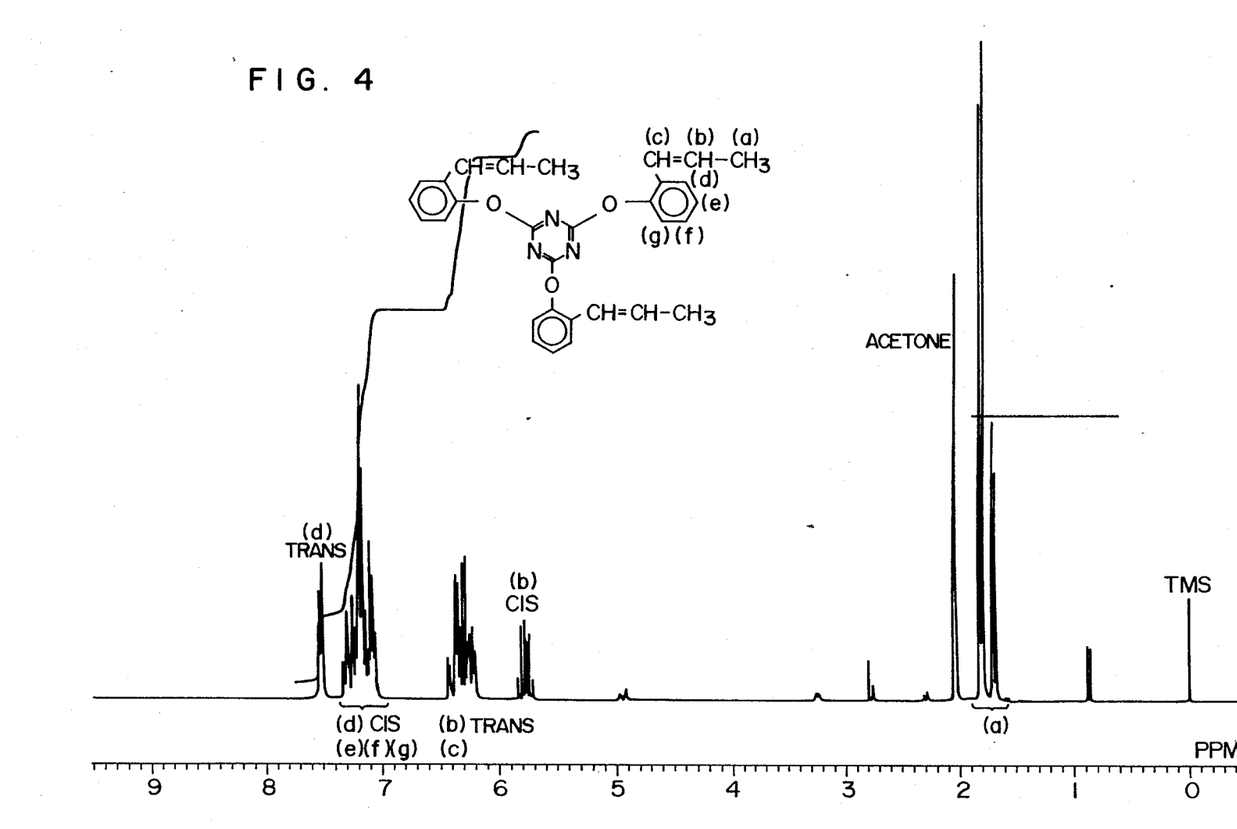
FIG. 4 shows an NMR spectrum of a compound prepared in Example 2.
Figure 5:
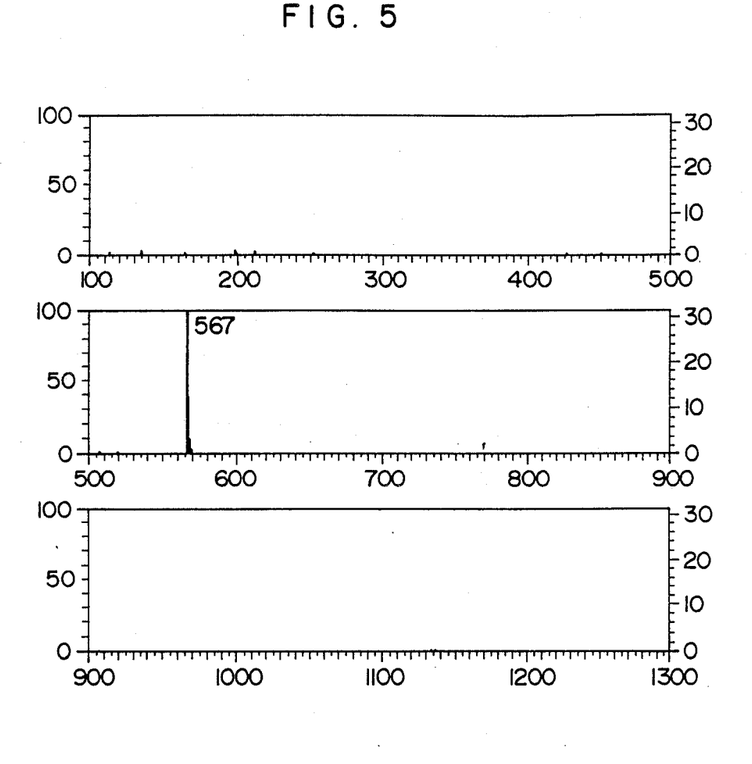
FIG. 5 shows FD-MS spectra of compounds prepared in Example 3.
Figure 6:
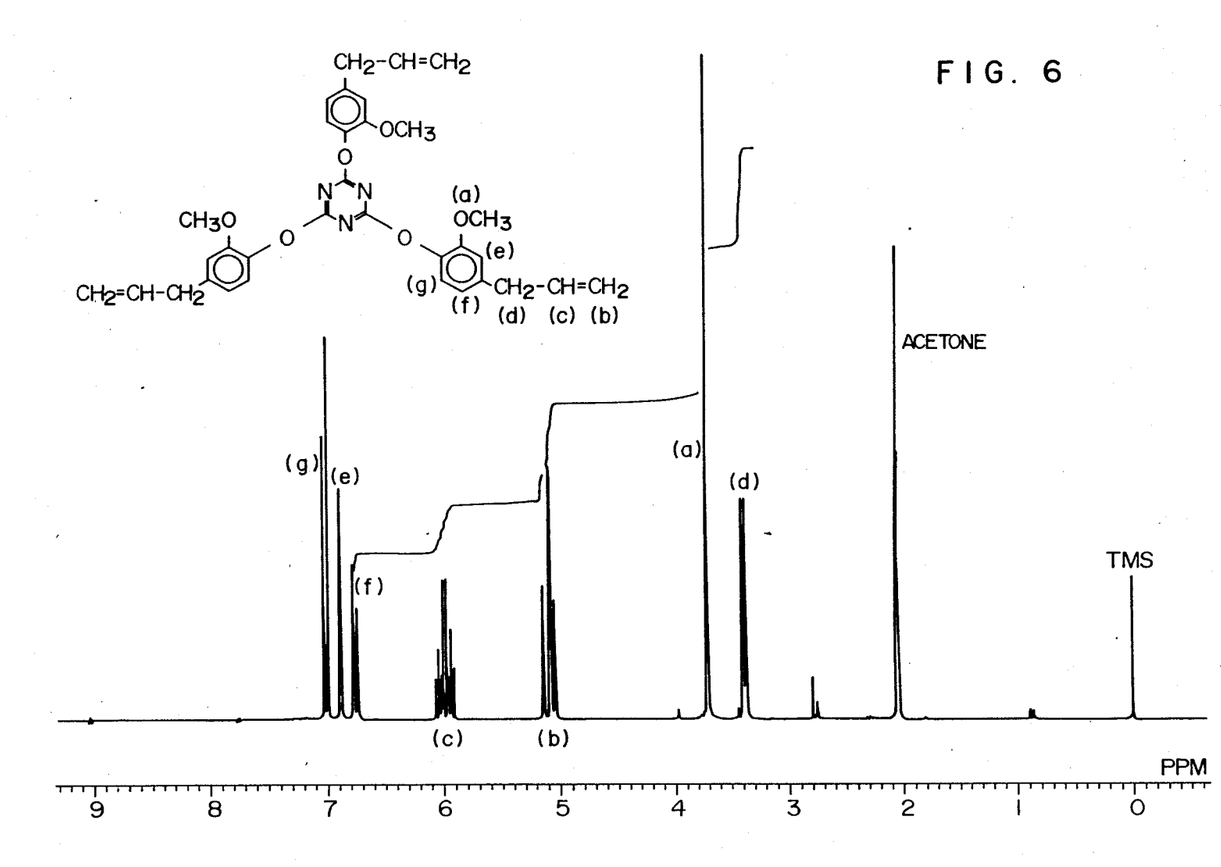
FIG. 6 shows an NMR spectrum of a compound prepared in Example 3.

Of the s-triazine compounds, which are each a component of the present inventive resin composition, having at least two alkenylaryoxy groups in the molecule, a crystalline s-triazine compound is constituted mainly of a compound represented by the general formula $$\begin{array}{c} Y \\ N \overset{\|}{\diagup} N \\ Ar_1O \diagdown N \diagup OAr_1 \end{array} \quad (2)$$

wherein $Ar_1$ and Y are as defined above. That is, $Ar_1$ is at least one residue represented by

[structure: phenyl ring with X substituent]

X being an alkenyl group exemplified by $CH_2=CH—$, $$CH_2=\overset{CH_3}{\underset{|}{C}}—,$$

$CH_2=CHCH_2—$, $$CH_2=\overset{CH_3}{\underset{|}{C}}—CH_2—,$$

and $CH_3CH=CH—$. A compound of formula (2) wherein X of $Ar_1$ is $$CH_2=\overset{CH_3}{\underset{|}{C}}—$$

is publicly known. As a result of investigation of crystalline s-triazine compounds, the present inventors have found that the compound of formula (2) wherein X of $Ar_1$ is $CH_2=CH.CH_2—$ or $CH_3CH=CH—$ gives a thermosetting resin especially superior in moldability.

When the known compound having

$$CH_2=\overset{CH_3}{\underset{|}{C}}—$$

as X is used, the resulting thermosetting resin composition is hardened too quickly, hence being much inferior in workability for curing and molding. In contrast when X is $CH_2=CHCH_2—$ or $CH_3CH=CH—$, in the com- pound represented by formula (2), the resulting resin composition has been found to exhibit a moderate rate of hardening and excellent workability, i.e. moldability. In formula (2), Y may be the above defined or another group or atom, for example, alkyl, alkoxy, halogen, amino substituted or unsubstituted by one or two alkyl groups, aryl, aryloxy, hydroxyl, or $CH_2=CH-CH_2O-$. The aromatic ring of is allowed to have other substituents besides X. Of the other substituents, particularly preferred are, for example, $C_1-C_5$ alkyl groups and $C_1-C_5$ alkoxy groups.

The s-triazine compounds of the present invention may include those having two or more triazine rings combined together. In particular when resin A is used, the resulting resin composition is excellent in processability and workability. That is, resin A is a noncrystalline compound having no definite melting point and flows at temperatures below 100° C. In consequence, when used jointly with other ingredients, particularly with the polymaleimide compound, resin A makes it possible to knead them at low temperature and brings about great improvements of the resulting resin composition in processability and workability.

Resin A is described below in more detail.

At least 20% of resin A should be occupied by components of formula (1) wherein n is at least 1. When containing more than 80% of the component of n=0, such a resin will be crystalline. In order to flow such a crystalline resin, it is necessary to heat the resin at a temperature of at least 100° C.

Examples of $Ar_1$ in formula (1) are the same as those of $Ar_1$ in formula (2). Two or more radicals examplified above can be contained in one molecule. (In other words, $Ar_1$'s in formula (1) are the same or different). Examples of Y in formula (1) are also the same as those of Y in formula (2). Preferred radicals as Y in formula (1) are alkyl, alkoxy, aryl, aryloxy, and $CH_2=CH-CH_2O$. For high heat resistance, it is most desirable that Y be $-OAr_1$. On the other hand, $Ar_2$ is a residue of divalent phenol, for example,

-continued

-continued or a mixture of these residues. Aromatic rings of these phenols may have other substituents beside the hydroxyl group.

The s-triazine compound of the present invention can be prepared as follows:

The s-triazine compound in crystalline form is prepared, for instance, by reacting 2 moles of alkenylphenol with 1 mole of a compound represented by the formula

(Y is as defined above) in the presence of a base. This base is exemplified by sodium hydroxide, potassium hydroxide, sodium carbonate, potassium carbonate, sodium methylate, sodium ethylate, triethylamine, diethylamine, and pyridine. When Y is also an alkenylphenoxy group, such an s-triazine compound can be prepared by reacting 3 moles of the corresponding alkenylphenol with 1 mole of cyanuryl chloride, which is represented by the formula in the presence of a base. Though the preparation method is not limited to this.

The s-triazine compound in noncrystalline form, i.e. resin A can be prepared, for instance, as follows: When Y of formula (1) is —OAr$_1$, such an s-triazine compound can be prepared by reacting (n+1) moles of cyanyryl chloride with n mole(s) of a divalent phenol represented by HO—Ar$_2$—OH and (n+3) moles of an alkenyl phenol preferably at a temperature of 0° to 100° C., preferably in the presence of a base. The base is exemplified by sodium hydroxide, potassium hydroxide, sodium carbonate, potassium carbonate, sodium methylate, sodium ethylate, triethylamine, diethylaniline, and pyridine. To react with cyanuryl chloride, either of the divalent phenol and the alkenyl phenol may be added prior to the other or they may be added at the same time.

When Y is alkyl, aryl, alkoxy, or aryloxy, it is desirable that a dichlorotriazine represented by the formula wherein W is alkyl, aryl, alkoxy, or aryloxy be prepared previously and then (n+1) moles of this dichlorotriazine be reacted with n mole(s) of a divalent phenol and 2 moles of an alkenylphenol. For example, the same reaction conditions as in the case where Y is —OAr$_1$ may be applied.

The compound represented by formula (3) can be prepared in the following way: When W is alkyl or aryl, such a monosubstituted dichloro-s-triazine can be obtained by reacting cyanuryl chloride with the corresponding Grinard reagent. When W is alkoxy or aryloxy, such a dichloro-s-triazine can be prepared by reacting cyanuryl chloride with the corresponding alcohol or phenol.

The method for resin A preparation is not limited to those described above.

Another component, polymaleimide, of the resin composition of the present invention is a compound having at least two maleimide groups represented by the formula wherein R$_1$ is hydrogen or lower alkyl, in the molecule.

Such polymaleimides include, for example, N,N'-diphenylmethane bismaleimide, N,N'-phenylenebismaleimide, N,N'-(diphenyl ether)bismaleimide, N,N'-(diphenyl sulfone)bismaleimide, N,N'-dicyclohexylmethanebismaleimide, N,N'-xylenebismaleimide, N,N'-tolylenebismaleimide, N,N'-benzophenonebismaleimide, N,N'-diphenylpropanebismaleimide, N,N'-(diphenyl sulfide)bismaleimide, N,N'-xylylenebismaleimide, N,N'-diphenylcyclohexanebismaleimide, N,N'-dichlorodiphenylmethanebismaleimide, N,N'-diphenylmethanebismethylmaleimide, N,N'-(diphenyl ether)bismethylmaleimide, N,N'-(diphenyl sulfone) bismethylmaleimide (each of these compounds includes isomers), N,N'-ethylenebismaleimide, N,N'-hexamethylenebismaleimide, N,N'-hexamethylenebismethylmaleimide, N,N'-hydroxypropylenebismaleimide, and further prepolymers terminated by N,N'-bismaleimide skeletons prepared by addition of diamines to these N,N'-bismaleimide compounds, aminophenyl-1,3,3-trimethylaminoindane, bisaminophenoxybenzene, 2,2-bisaminophenoxydiphenyl propane, 4,4-bisaminophenoxy diphenyl sulfone (each of these compounds includes isomers), maleimidation or methylmaleimidation products of aniline-formalin polycondensates, and mixtures of all the compounds cited above.

In the present invention, the mixing ratio of the s-triazine compound to the polymaleimide can be varied over a wide range. Preferably they are mixed so that the quantity of the maleimide group will range from 0.4 to 3 equivalents per 1 equivalent of the alkenyl group. When either the s-triazine compound or the polymaleimide compound is extremely in excess of the other, the curability and heat resistance of the resin composition will be lowered.

The thermosetting resin composition of the present invention can be readily cured by heating without any catalyst and can also be cured by heating in the presence of a radical polymerization initiator such as an organic peroxide or an azo compound. Such radical polymerization initiators include, for example, benzoyl peroxide, di-t-butyl peroxide, dicumyl peroxide, lauroyl peroxide, acetyl peroxide, methyl ethyl ketone peroxide, cyclohexanone peroxide, t-butyl hydroperoxide, and azobisisobutyronitrile. These initiators can also be used each jointly with; a tertiary amine such as tributylamine, triethylamine, or triamylamine; quaternary ammonium salt such as benzyltriethylammonium chloride or benzyltrimethylammonium hydroxide; imidazole compound, boron trifluoride complex, or transistion metal acetylacetonate. Suitable temperatures for the curing are 50° to 300° C.

It is also possible to use a known polymerization inhibitor additionally for the purpose of controlling the rate of curing. Such polymerization inhibitor include; phenols, e.g. 2,6-di-t-butyl-4-methylphenol, 2,2'-methylenebis(4-ethyl-6-t-butylphenol), 4,4'-methylenebis(2,6-di-t-butylphenol), 4,4'-thiobis(3-methyl-6-t-butylphenol), and hydroquinone monomethyl ether; polyhydric phenols, e.g. hydroquinone, catechol, p-t-butylcatechol, 2,5-di-t-butylhydroquinone, methylhydroquinone, t-butylhydroquinone, and pyrogallol; phenothiazine compounds, e.g. phenothiazine, benzophenothiazine, and acetamidophenothiazine; and N-nitrosoamine compounds, e.g. N-nitrosodiphenylamine and N-nitrosodimethylamine.

The composition of the present invention contains, if necessary, an extender, filler, reinforcement, pigment, or the like. Such additives include, for example, powders of silica, calcium carbonate, antimony trioxide, kaolin, titanium dioxide, zinc oxide, mica, baryte, carbon black, polyethylene, polypropylene, aluminum, iron, and copper and fibers of glass, carbon, alumina, and asbestos. Compounds with these additives are used for moldings, laminates, adhesives, composite materials, etc. According to applications, the present resin composition may contain other thermosetting resins, for example, alkenyl-containing or triazine ring-containing resins, unsaturated polyester resins, epoxy resins, silicone resins, and phenol resins other than the present inventive resin. Thus, the present inventive resin composition exhibits excellent processability, heat resistance, mechanical properties, and electrical properties.

The thermosetting resin composition of the present invention, combined with an inorganic filler, can be used particularly as an excellent encapsulant. Suitable inorganic fillers for this purpose include powdered silica, alumina, talc, calcium carbonate, titanium white, clay, asbestos, iron oxide red, and glass fiber. In particular, powdered silica and alumina are preferable. The mixing proportion of such an inorganic filler needs to be in the range of 25 to 90%, preferably 60 to 80%, by weight based on the whole resin composition.

The resin composition for encapsulant of the present invention may contain a known epoxy resin and a hardener for it. Examples of such epoxy resins are; novolak-based epoxy resins derived from novolak resins that are reaction products a formaldehyde with phenols such as phenol and cresol; glycidyl ether compounds derived from trivalent or higher-valent phenols such as phloroglucin, tris(4-hydroxyphenyl)methane, and 1,1,2,2-tetrakis(4-hydroxyphenyl)ethane; diglycidyl ether compounds derived from divalent phenols such as bisphenol A, bisphenol F, hydroquinone, and resorcinol or from halogenated bisphenols such as tetrabromobisphenol A; amine type epoxy resins derived from p-aminophenol, m-aminophenol, 4-amino-m-cresol, 6-amino-m-cresol, 4,4'-diaminodiphenylmethane, 3,3'-diaminodiphenylmethane, 4,4'-diaminodiphenyl ether, 3,4'-diaminodiphenyl ether, 1,4-bis(4-aminophenoxy)benzene, 1,4-bis(3-aminophenoxy)benzene, 1,3-bis(4-aminophenoxy)benzene, 1,3-bis(3-aminophenoxy)benzene, 2,2-bis(4-aminophenoxyphenyl)propane, p-phenylenediamine, m-phenylenediamine, 2,4-tolylenediamine, 2,6-tolylenediamine, p-xylylenediamine, m-xylylenediamine, 1,4-cyclohexane-bis(methylamine), and 1,3-cyclohexane-bis(methylamine); glycidyl ester compounds derived from aromatic carboxylic acids such as p-hydroxybenzoic acid, m-hydroxybenzoic acid, terephthalic acid, and isophthalic acid; hydantoin type epoxy resins derived from 5,5-dimethylhydantoin and the like; alicyclic epoxy resins from 2,2-bis(3,4-epoxycyclohexyl)propane, 2,2-bis]4-(2,3-epoxypropyl)cyclohexyl]propane, vinylcyclohexene dioxide, 3,4-epoxycyclohexylmethyl-3,4-epoxycyclohexanecarboxylate, and the like; resins of N,N-diglycidylaniline and the like; and mixtures of these resins.

Suitable hardeners for the epoxy resin include, though not limited to; novolak resins, e.g. phenol novolak and cresol novolak; aromatic polyamines, e.g. diaminodiphenylmethane and diaminodiphenyl sulfone; and acid anhydrides, e.g. pyromellitic anhydride and benzophenonetetracarboxylic anhydride.

In addition, the resin composition for encapsulant of the present invention contains, if necessary, a mold releasing agent such as a natural or synthetic wax, higher fatty acid, its metal salt, or paraffin, a colorant such as carbon black, a coupling agent, and a flame retardant such as antimony trioxide, phosphorus compound, or brominated epoxy resin.

The resin composition for encapsulant of the invention is superior to conventional heat resistant resin compositions in processability, heat resistance, and electrical properties and hence is very useful as a material for encapsulant.

Resin A of the invention can also be used for purposes other than thermosetting resin compositions. Resin A is curable by heating in single form as well as in combination with an unsaturated compound or resin other than polymaleimide. The unsaturated compound or resin is exemplified by unsaturated polyester resins, diallyl phthalate resins, epoxyacrylate resins, and compounds or resins other than the present inventive resin which have two or more alkenyl groups in the molecule, but is not limited to these examples.

The following examples illustrate the present invention in more detail without limiting the scope of the invention.

PREPARATION EXAMPLE 1

A four-necked flask equipped with a stirrer, thermometer, and dropping funnel was charged with 25.8 g (0.14 mole) of cyanuryl chloride, 56.4 g (0.42 mole) of m-isopropenylphenol, and 140 g of acetone and a solution was prepared therefrom. Then, 176 g of 10% aqueous NaOH (0.441 mole) was added dropwise to the solution over 1 hour while maintaining the mixture at room temperature. This mixture was further kept at the same temperature for 1 hour. Then, the product was taken out, washed with water, and dried, giving a compound of the following character:

M.P.: 129°–131° C.

Anal., Found (%): C, 75.8; H, 5.65; N, 8.84.

From these data combined with the results of FD-MS and NMR, this compound was identified as tris(m-isopropenylphenoxy)-s-triazine (hereinafter designated as IPT).

EXAMPLE 1

A compound of the following character was prepared according to the procedure of preparation Example 1 but using O-allylphenol in place of m-isopropenylphenol.

M.P.: 108°–110° C.

Anal., Found (%): C, 75.6; H, 5.73; N, 8.70.

Therefrom and from the results of FD-MS and NMR, this compound was identified as tris(O-allylphenoxy)-s-triazine (hereinafter designated as APT).

EXAMPLE 2

A four-necked flask equipped with a stirrer, thermometer, and dropping funnel was charged with 12.9 g (0.07 mole) of cyanuryl chloride, 28.2 g (0.21 mole) of O-propenylphenol, and 70 g of acetone and a solution was prepared therefrom. Then, 88.2 g of 10% aqueous NaOH (0.221 mole) was added dropwise to the solution over 1 hour while maintaining the mixture at room temperature. This mixture was further kept at the same temperature for 1 hour. Then, the product was taken out, washed with water, and dried, giving a compound of the following character:

M.P.: 123°–126° C.

Anal., Found (%): C, 75.8; H, 5.81; N, 8.77.

From these data combined with the results of FD-MS and NMR, this compound was identified as tris(O-propenylphenoxy)-s-triazine (hereinafter designated as PPT).

EXAMPLE 3

A four-necked flask equipped with a stirrer, thermometer, and dropping funnel was charged with 12.9 g (0.07 mole) of cyanuryl chloride, 34.5 g (0.21 mole) of 4-allyl-2-methoxyphenol, and 80.7 g of acetone and a solution was prepared therefrom. Then, 88.2 g of 10% aqueous NaOH (0.221 mole) was added dropwise to the solution over 1 hour while maintaining the mixture at room temperature. This mixture was further kept at the same temperature for 1 hour. Then, the product was taken out, washed with water, and dried, giving a compound of the following character:

M.P.: 131°–133° C.

Anal., Found (%): C, 69.5; H, 5.79; N, 7.45.

From these data combined with the results of FD-MS and NMR, this compound was identified as tris(4-allyl-2-methoxyphenoxy)-s-triazine (hereinafter designated as AMPT).

EXAMPLES 4–6 and Comparative Example 1

The gel time of resin compositions shown in Table 1 were measured. The results are shown in Table 1.

TABLE 1

| | Example 4 | Example 5 | Example 6 | Comparative Example 1 |
|---|---|---|---|---|
| Resin composition | | | | |
| APT | 100 | — | — | — |
| PPT | — | 100 | — | — |
| AMPT | — | — | 100 | — |
| IPT | — | — | — | 100 |
| BMI* | 169 | 169 | 142 | 169 |
| Gel time (at 180° C.) | 4'20" | 1'10" | 3'40" | <30" |

The compositions of the resins are given in parts by weight.
*N,N'-4,4'diphenylmethanebismaleimide, diphenylmethanebismaleimide (hereinafter designed as BMI) supplied by Sumitomo Chemicals, Co., Ltd.

As is evident from Table 1, in case of APT, PPT and AMPT, the gel time of the resin composition containing any of them is longer than that of the resin composition containing IPT. Thus, an uneven reaction hardly occur and an easy thermosetting can be expected in case of them.

EXAMPLES 7–8 AND COMPARATIVE EXAMPLE 2

Cured products were prepared under conditions as shown in Table 1 by using compounds obtained in Preparation Example 1, Example 1 and 2,2'-diallylbisphenol A as a control in combination with BMI supplied by Mitsui Toatsu Chemicals, Inc.

Properties of the cured products are also shown in Table 2. It can be seen that compositions of the present invention are well balanced among curability, heat resistance, and mechanical properties.

TABLE 2

| | | Example 7 | Example 8 | Comparative Example 2 |
|---|---|---|---|---|
| Ratio between double bonds* | | 1/2 | 1/1.5 | 1/1.25 |
| IPT | | 100 | — | — |
| APT | | — | 100 | — |
| 2,2'-Diallylbisphenol A | | — | — | 100 |
| BMI | | 224 | 168 | 145 |
| Methylhydroquinone | | 6.5 | — | — |
| Curing conditions | Press** | 150° C. × 1 hr | 180° C. × 1 hr | 200° C. × 1 hr |
| | Post-curing | 230° C. × 8 hr | 230° C. × 8 hr | 230° C. × 8 hr |
| Tg (°C.)*** | | 302 | 294 | 263 |
| Pyrosis temperature (°C.) | in $N_2$ | 417 | 415 | 415 |
| | in air | 412 | 411 | 410 |
| Flexural strength (kg/mm$^2$) | | 15.5 | 15.8 | 13.9 |
| Flexural modulus (kg/mm$^2$) | | 452 | 448 | 412 |

Figures for IPT, APT, 2,2'-Diallylbispenol A, BMI and Methylhydroquinone are given in parts by weight.
*Molar ratio of alkenyl groups/maleimido groups
**Pressure 50 kg/cm$^2$
***According to the TMA method

EXAMPLE 9

A flask equipped with a stirrer, thermometer, and dropping funnel was charged with 53.6 g (0.4 mole) of 2-propenylphenol, 36.8 g (0.2 mole) of cyanuryl chloride, 11.0 g (0.1 mole) of resorcinol, and 173 g of acetone, and a solution was prepared therefrom. Then, 252.0 g of 10% aqueous NaOH (0.63 mole) was added dropwise to the solution over 1 hour while maintaining the mixture at temperatures of 20° to 30° C. This mixture was further kept at the same temperatures for 2 hours to complete the reaction. Thereafter, methyl isobutyl ketone was added, and the mixture was washed with water to remove the by-product NaCl, and the solvents were distilled off, giving a resin (hereinafter designated as Resin A-1) having a softening point of 58° C.

The molecular weight distribution was examined by GPC (solvent: tetrahydrofuran; detector: RI; columns: G 3000-HXL, 2000-HXL, and 1000-HXL, supplied by Toyo Soda Mfg. Co., Ltd.). From the results, 62% of this resin was found to consist of components represented by formula (1) having n values of at least 1.

EXAMPLE 10

A resin having a softening point of 89° C. was prepared according to the procedure of Example 9 but using 25.0 g (0.1 mole) of bisphenol S in place of 11.0 g (0.1 mole) of resorcinol (hereinafter designated as Resin A-2). From the results of GPC analysis, 80% of this resin was found to consist of components having n values of at least 1.

EXAMPLE 11

A flask equipped with a stirrer, thermometer, and dropping funnel was charged with 45.0 g (0.25 mole) of 2-methoxy-4,6-dichloro-s-triazine, 26.8 g (0.2 mole) of 2-allylphenol, 34.2 g (0.15 mole) of bisphenol A, and 187 g of dioxane, and a solution was prepared therefrom. Then, 210 g of 10% aqueous NaOH (0.525 mole) was added dropwise to the solution over 1 hour while maintaining the mixture at temperatures of 40° to 50° C. This mixture was further kept at the same temperatures for 2 hours to complete the reaction. Thereafter, the procedure of Example 9 was followed, giving a resin having a softening point of 78° C. (hereinafter designated as Resin A-3). GPC analysis indicates that 83% of this resin consists of components having n values of at least 1.

The 2-methoxy-4,6-dichloro-s-triazine used in this example was synthesized according to the method of J. T. Thurston et al. (J. Amer. Chem. Soc., 73, p. 2986 (1951)) using cyanuryl chloride, methanol, and sodium hydrogencarbonate as raw materials.

EXAMPLE 12

A flask equipped with a stirrer, thermometer, and dropping funnel was charged with 45.2 g (0.2 mole) of 2-phenyl-4,6-dichloro-s-triazine, 26.8 g (0.2 mole) of 3-isopropenylphenol, 11.0 g (0.1 mole) of resorcinol, and 160 g of acetone, and a solution was prepared therefrom. Then, 168.0 g of 10% aqueous NaOH (0.42 mole) was added dropwise to the solution over 1 hour while maintaining the mixture at temperatures of 40° to 50° C. This mixture was further kept at the same temperatures for 2 hours to complete the reaction. Thereafter, the procedure of Example 9 was followed, giving a resin having a softening point of 54° C. (hereinafter designated as Resin A-4). GPC analysis indicates that 56% of this resin consists of components having n values of at least 1.

The 2-phenyl-4,6-dichloro-s-triazine used in this example was synthesized according to the method of R. Hist et al. (Helo. Chim. Acta., 33, p. 1365 (1950)) using 1 mole of cyanuryl chloride and 1 mole of phenylmagnesium bromide as raw materials.

EXAMPLES 13–16

Using resins prepared in Examples 9–12 in combination with BMI (supplied by Sumitomo Chemical Co., Ltd.), cured products were prepared under conditions as shown in Table 3. Properties of the cured products are also shown in Table 3. It can be seen therefrom that compositions of the present invention are well balanced among curability, heat resistance, and mechanical properties.

All the resins prepared in Examples 9–12 have softening points of up to 100° C. and when mixed with BMI, can be kneaded over rolls at temperatures of up to 100° C., providing excellent processability and workability to the composition.

TABLE 3

| | Example 13 | Example 14 | Example 15 | Example 16 |
|---|---|---|---|---|
| Ratio between double bonds* | 1/1.7 | 1/1.7 | 1/2.2 | 1/2 |
| Resin A-1 | 100 | — | — | — |
| Resin A-2 | — | 100 | — | — |
| Resin A-3 | — | — | 100 | — |
| Resin A-4 | — | — | — | 100 |
| BMI | 153 | 130 | 89.8 | 105 |
| Curing conditions Press** | 170° C. × 1 hr | 170° C. × 1 hr | 170° C. × 1 hr | 170° C. × 1 hr |
| Curing conditions Post-curing | 230° C. × 8 hr | 230° C. × 8 hr | 230° C. × 8 hr | 230° C. × 8 hr |
| Tg (°C.)*** | 284 | 286 | 233 | 251 |
| Pyrosis temperature (°C.) in $N_2$ | 419 | 431 | 415 | 425 |
| Pyrosis temperature (°C.) in air | 411 | 430 | 420 | 431 |
| Flexural strength (kg/mm$^2$) | 15.6 | 16.7 | 17.3 | 13.4 |
| Flexural modulus (kg/mm$^2$) | 420 | 430 | 382 | 395 |

Figures for Resin A-1 to Resin A-4, and BMI are given in parts by weight.
*Molar ratio of alkenyl groups/maleimido groups
**Pressure 50 kg/cm$^2$
***According to the TMA method

EXAMPLES 17–19

Resin compositions were prepared by melt mixing materials selected from s-triazine compounds (IPT, APT) obtained in Preparation Example 1 and Example 1, BMI (supplied by Sumitomo Chemicals Co., Ltd.) and a curing accelerator, filler, mold releasing agent, and coupling agent in proportions as shown in Table 4 over hot rolls at temperatures of 50° to 120° C. for 5 minutes, followed by cooling and grinding the mixtures. Then, these compositions were transfer-molded at 200° C. and 70 kg/cm² for 10 minutes, and post-cured at 200° C. for 5 hours. Results of evaluating properties of the cured products are shown in Table 5.

COMPARATIVE EXAMPLE 3

A resin composition was prepared by melt mixing an o-cresol novolak type epoxy resin (epoxy equivalent weight: 195 g/eq), phenol novolak resin (OH equivalent weight: 110 g/eq), curing accelerator, filler, mold releasing agent, and coupling agent in proportions as shown in Table 4 according to the procedure of Examples 17–19. Then, the composition was transfer-molded at 175° C. and 70 kg/cm² for 5 minutes, and post-cured at 180° C. for 5 hours. Results of evaluating properties of the cured product are shown in Table 5.

TABLE 4

| Ingredient | Example | | | Comparative Example |
|---|---|---|---|---|
| Example No. | 17 | 18 | 19 | 3 |
| IPT | 100 | — | — | — |
| APT | — | 100 | 100 | — |
| BMI | 225 | 225 | 225 | — |
| Epoxy resin a | — | — | 36 | — |
| Epoxy resin b | — | — | — | 100 |
| Phenol novolak resin | — | — | — | 56 |
| Dicumyl peroxide | — | 3.9 | 3.9 | — |
| DBU | — | — | — | 2 |
| Fused silica | 784 | 784 | 871 | 376 |
| Carnauba wax | 3.2 | 3.2 | 3.6 | 1 |
| Aminosilane coupling agent | 4.1 | 4.1 | 4.6 | — |

TABLE 4-continued

| Ingredient | Example | | | Comparative Example |
|---|---|---|---|---|
| Example No. | 17 | 18 | 19 | 3 |
| Epoxysilane coupling agent | — | — | — | 2 |

Notes:
Figures in this table are given in parts by weight.
Epoxy resin a: Sumiepoxy ESCN 220 HH, supplied by Sumitomo Chemical Co., Ltd. (epoxy equivalent weight: 217 g/eq)
Epoxy resin b: Sumiepoxy ESCN-195XL, supplied by Sumitomo Chemical Co., Ltd. (epoxy equivalent weight: 195 g/eq)
Fused silica: Hisilex EF-10, supplied by Hayashi Kasei Co., Ltd.
Aminosilane coupling agent: A-1100, supplied by Nihon Unicar Co., Ltd.
Epoxysilane coupling agent: SH-6040, supplied by Toray Silicone Co., Ltd.

TABLE 5

| Property | Example | | | Comparative Example |
|---|---|---|---|---|
| Example No. | 17 | 18 | 19 | 3 |
| Tg* (°C.) | 285 | 265 | 250 | 162 |
| Linear coefficient of expansion (<Tg)* × 10⁵ °C.⁻¹ | 1.7 | 1.7 | 1.8 | 2.3 |
| Retention (%) of elastic modulus** (relatives to 20° C. value) 100° C. | 95 | 95 | 95 | 93 |
| 200° C. | 85 | 85 | 80 | 29 |
| 260° C. | 79 | 75 | 71 | 11 |
| Volume resistivity (Ω-cm) normal state | 2.0 × 10¹⁶ | 2.0 × 10¹⁶ | 1.8 × 10¹⁶ | 2.1 × 10¹⁶ |
| 100° C. | 1.3 × 10¹⁶ | 1.2 × 10¹⁶ | 8.4 × 10¹⁶ | 1.2 × 10¹⁶ |
| 150° C. | 9.5 × 10¹⁴ | 9.0 × 10¹⁴ | 1.0 × 10¹⁵ | 3.4 × 10¹⁴ |
| 180° C. | 3.8 × 10¹⁴ | 3.1 × 10¹⁴ | 3.5 × 10¹⁴ | 3.7 × 10¹³ |

*TMA method (Thermal analyzer, DT-40, supplied by Shimazu Co.)
**TMA method (Rheograph Solid, supplied by Toyo Seiki Co., Ltd.)

As are evident from Table 5, cured products from compositions of the present invention have excellent heat resistance and electric insulation resistance.

What is claimed is:

1. A resin represented by the general formula (1)

wherein, n denotes numbers of 0 to 15, $Ar_1$ denotes a monovalent alkenylphenol residue, $Ar_2$ denotes a divalent phenol residue, and Y denotes —$OAr_1$ or another substituent, at least 20% of said resin consisting of components having n values of at least 1.

2. The resin of claim 1, wherein the alkenyl group of the alkenylphenol residue is propenyl, isopropenyl, or allyl.

* * * * *